United States Patent [19]

Lentsch

[11] Patent Number: 5,116,543
[45] Date of Patent: May 26, 1992

[54] WHOLE BODY CLEANING AGENT CONTAINING N-ACYLTAURATE

[75] Inventor: Steven E. Lentsch, St. Paul, Minn.

[73] Assignee: The United States of America as represented by the administrator of the National Aeronautics and Space Administration, Washington, D.C.

[21] Appl. No.: 529,427

[22] Filed: May 29, 1990

[51] Int. Cl.$^5$ .................. C11D 1/28; A61K 7/075; C02F 1/00; E03D 1/00
[52] U.S. Cl. .................. 252/545; 252/547; 252/DIG. 5; 252/DIG. 14; 252/DIG. 13; 424/70; 4/661; 4/665; 4/DIG. 9; 134/10; 210/660
[58] Field of Search .................. 252/545, 547, DIG. 5, 252/DIG. 14, DIG. 13; 4/603, 619, DIG. 9, 665; 134/10; 240/660; 23.1/424; 23.2/70

[56] References Cited

U.S. PATENT DOCUMENTS

| | | |
|---|---|---|
| 2,874,125 | 2/1959 | Lew .................. 252/545 |
| 2,921,030 | 1/1960 | Stayner et al. .................. 252/545 |
| 3,671,634 | 6/1972 | Carlson et al. .................. 424/274 |
| 3,779,929 | 12/1973 | Abler et al. .................. 252/90 |
| 3,862,307 | 1/1975 | Di Guillo .................. 424/52 |
| 3,981,677 | 9/1976 | Halasz et al. .................. 8/10.2 |
| 4,110,263 | 8/1978 | Lindemann .................. 252/545 |
| 4,198,316 | 4/1980 | Nahta .................. 252/354 |
| 4,239,631 | 12/1980 | Brown .................. 252/8.75 |
| 4,290,904 | 9/1981 | Poper et al. .................. 252/118 |
| 4,295,985 | 10/1981 | Petrow et al. .................. 252/105 |
| 4,385,413 | 5/1983 | Goldsmith .................. 15/32 |
| 4,440,295 | 4/1984 | Blackwood-Murray et al. .................. 198/843 |
| 4,478,853 | 10/1984 | Chaussee .................. 424/358 |
| 4,556,510 | 12/1985 | Holsopple .................. 252/547 |
| 4,606,839 | 8/1986 | Harding .................. 252/132 |
| 4,617,148 | 10/1986 | Shields .................. 252/547 |
| 4,673,525 | 6/1987 | Small et al. .................. 252/132 |
| 4,774,016 | 9/1988 | Gazzani .................. 252/170 |
| 4,780,249 | 10/1988 | Pittz et al. .................. 252/547 |
| 4,784,849 | 11/1988 | Tutsky .................. 424/73 |
| 4,828,709 | 5/1989 | Houser et al. .................. 210/669 |
| 4,954,282 | 9/1990 | Rys et al. .................. 252/117 |

FOREIGN PATENT DOCUMENTS 917496 2/1963 European Pat. Off. .
61-272295 12/1986 Japan .

OTHER PUBLICATIONS

Benjamin Levitt, F.A.I.C., Oils, Detergents and Maintenance Specialties, 1967, pp. 39-40.
Fact Sheet, GAF Corporation *IEGPON TC*-42 (Anionic) 140 W. 51 St., New York, N.Y. 10020.
Fact Sheet, Calimar, Inc., *REALEX HVD High-Viscosity Dispenser*, 40 Stirling Rd., Watchung, N.J. 07060.

*Primary Examiner*—Paul Lieberman
*Assistant Examiner*—Erin M. Higgins
*Attorney, Agent, or Firm*—Edward K. Fein; Guy M. Miller; Russell E. Schlorff

[57] ABSTRACT

A whole body cleansing agent for bathing with a small quantity of water in microgravity conditions which consists essentially of a paste comprising an acyltaurate, a skin conditioner, a hair conditioner, and a preservative. Also disclosed is a method of bathing with a small quantity of water which includes the steps of wetting the skin and hair with a small quantity of water, lathering the skin with the paste, rinsing the lather from the skin and hair with a small quantity of water to produce a rinse water containing the cleansing agent, defoaming the rinse water and supplying the defoamed rinse water to a water reclamation unit for recycle thereof.

11 Claims, No Drawings

WHOLE BODY CLEANING AGENT CONTAINING N-ACYLTAURATE

ORIGIN OF THE INVENTION

The invention described herein was made in the performance of work under a NASA contract and is subject to provisions of §305 of the National Aeronautics and Space Act of 1958, Public Law 85-568 (72 Stat. 435; 42 U.S.C. §2457).

TECHNICAL FIELD OF THE INVENTION

The invention relates to whole body cleansing agents, and particularly to such cleansing agents suitable for use in bathing with small quantities of water which is reclaimed, such as in long duration space travel.

BACKGROUND OF THE INVENTION

Travel in space for a relatively long duration imposes a unique set of requirements for the bathing of crew members. In addition to the primary reason for bathing which is to satisfy the physiological, psychological and social needs of the crew throughout the duration of duty in a space vehicle, the cleansing agent utilized in bathing must also be compatible with any water reclamation system used to purify and recycle the water used for bathing.

Initial considerations in developing a suitable whole body cleansing agent for use on a space station involve the recognition of the criticality of using a minimum quantity of resources. Thus, bathing is performed using a minimum quantity of water and employing a single cleansing agent suitable for use on the skin as well as the hair. Low water usage of about 4 liters per shower is a key objective.

Since the system uses deionized water, particular attention must be paid to rinseability. For example, conventional solid soaps become very difficult to rinse in deionized water. Also, to simplify housecleaning, the cleansing agent should not leave a film on surfaces of the shower. Since unnecessary weight should desirably be eliminated, a concentrated form of cleansing agent is also desired.

Water reclamation systems used on space stations generally require that the water being reclaimed is low foaming since such equipment will not generally function properly with high foaming solutions. On the other hand, cleansing agent consumption increases drastically if the cleansing agent does not foam, and one's perception of cleanliness is low if foam levels are low.

Water reclamation can be complicated by the presence of unnecessary ingredients typically found in commercial liquid shampoos for providing a consumer-attractive form, fragrance and appearance. Water reclamation would be simplified if the cleansing agent contained 4 or fewer ingredients.

It is known that water does not drip or run off the body during a microgravity shower, making it more difficult to rinse the cleansing agent, especially from the hair. Microgravity conditions also require special attention to potential eye irritation by the cleansing agent because it is more difficult to rinse the cleansing agent from the eyes under microgravity conditions. In addition, high viscosity, concentrated cleansing agents are generally more irritating to the eyes and are more difficult to remove therefrom by blinking.

Because the whole body cleansing agent is applied in microgravity conditions, it should be very viscous to facilitate dispensing and application. The cleansing agent should lather effectively to a high-volume, stable and thick foam structure. Inadequate foaming leads to excessive use and does not provide a feeling of cleanliness thereafter. Foaming also facilitates spreading of the lather, efficient soil removal, and rinsing of the cleansing agent from the body.

On the other hand, as earlier stated, a water reclamation unit will not function properly with high foaming solutions.

In addition to the foregoing special considerations in microgravity, low-water-consumption considerations, the cleansing agent must perform the usual functions of soap and shampoo, providing a good feel on the skin and hands, clean and fresh-smelling hair, good hair luster, ease of combing wet hair, speed of drying of the hair, ease of combing and setting of dry hair, good control of dandruff, good odor of the cleansing agent, good residual odor on the body following use of the cleansing agent, must be non-toxic, non-irritating to the skin, non-irritating to the eyes, nonallergenic, and must not cause dermatitis or skin defatting.

As far as applicant is aware, no such cleansing agent has heretofore been available which meets the criteria for a suitable whole body cleansing agent for use in a shower system aboard a space station.

STATEMENT OF THE INVENTION

The present invention provides a whole body cleansing agent for bathing with a small quantity of water in microgravity conditions. The cleansing agent consists essentially of a paste comprising: (a) N-acyltaurate of the formula:

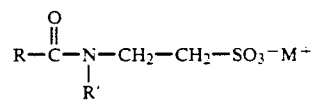

wherein the acyl group of which R is a part has from about 6 to about 20 carbon atoms, R' is hydrogen, lower alkyl of from 1 to 8 carbon atoms or cycloalkyl of from 5 to about 10 carbon atoms, and $M^+$ is a non-toxic water soluble cation; (b) a conditioner or conditioners in amounts effective for conditioning the skin and to condition the hair; (c) a preservative in an amount effective to preserve the taurate and the conditioners; and (d) water in an amount effective to form a paste. The paste is latherable to a foam which is defoamable by a defoaming agent. The paste is also readily rinseable with soft water, has a pH compatible with the skin and hair, and facilities water reclamation. The acyl group of which R is a part preferably has from about 10 to about 18 carbon atoms and R' is preferably hydrogen, methyl or cyclohexyl. $M^+$ is preferably ammonium, lithium, sodium or potassium. The taurate preferably comprises N-methyl-N-cocoyl taurate. The taurate preferably comprises from about 15 to about 25 percent by weight of the paste. The skin conditioner preferably comprises lecithin present in an amount from about 0.1 to about 3 percent by weight of the paste. The hair conditioner preferably comprises a polymeric quaternary ammonium salt in an amount of from 0.1 to about 3 percent by weight of the paste. The preservative is preferably formaldehyde present in an amount of from about 0.01 to about 1 percent by weight of the paste. The paste consists further essentially of water in an amount whereby the paste consistency of the formulation is formed. The paste preferably has a pH of from about 5 to about 7.

In another aspect, the present invention provides a method of bathing with a small quantity of water. The method comprises the steps of:

(a) wetting the skin and hair with a small quantity of water;
(b) lathering the wetted skin and hair with a whole body cleansing agent comprising a formulation of paste consistency consisting essentially of:
 (i) acyltaurate of the formula:

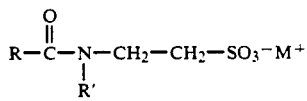

wherein the acyl group of which R is a part has from about 6 to about 20 carbon atoms, R' is hydrogen, lower alkyl or lower cycloalkyl and $M^+$ is a non-toxic water soluble cation;
 (ii) conditioner(s) for the skin and hair, and
 (iii) a preservative;
(c) rinsing the lather from the skin and hair with a small quantity of water to produce rinse water containing the cleansing agent;
(d) defoaming the rinse water; and
(e) supplying the defoamed rinse water to a water reclamation system for recycle thereof, said steps effectively cleansing the skin and hair with a maximum quantity of about 10 liters of water, preferably about 4 liters of water.

In a further aspect, the present invention provides a whole body cleansing system. The system comprises: (a) a pressurized water source; (b) means for wetting and rinsing the skin and hair with water from the water source; (c) means for dispensing a paste consisting essentially of:
 (i) acyltaurate of the formula

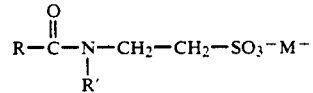

wherein the acyl group of which R is a part has from about 6 to about 20 carbon atoms, R' is hydrogen, lower alkyl or lower cycloalkyl and $M^+$ is a non-toxic water soluble cation;
 (ii) conditioner(s) for the skin and hair, and
 (iii) a preservative;
(d) means for recovering water and said paste from the skin and hair;
(e) means for defoaming the recovered water; and
(f) means for supplying the defoamed water to a water reclamation unit for recycling.

The recovering means may comprise a drain, particularly for gravity use, but preferably comprises a vacuum for microgravity conditions.

DETAILED DESCRIPTION OF THE INVENTION

The whole body cleansing agent in accordance with the present invention includes an N-acyltaurate, a skin conditioner, a hair conditioner and a preservative.

The N-acyltaurate component has the formula:

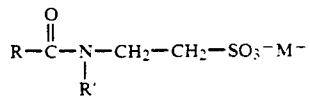

wherein the acyl group of which R is a part has from about 6 to about 20 carbon atoms, and is preferably an aliphatic acyl radical of from about 10 to about 18 carbon atoms (stated differently, R is hydrocarbyl of from about 5 to about 19 carbon atoms, preferably from about 9 to about 17 carbon atoms); R' is hydrogen, lower alkyl or lower cycloalkyl; and $M^+$ is a non-toxic water soluble cation. As suitable representative examples of acyl radicals of which R is a part, there may be mentioned hexoyl, heptoyl, decoyl, lauroyl, myristoyl, palmitoyl, steroyl, arachadoyl, behenoyl, lignoceroyl, cerotoyl, palmitoleoyl, oleoyl, vaccenoyl, linoleoyl, α-linolenoyl, arachidonoyl, cocoyl, and the like. By lower alkyl, it is meant that R' may be aliphatic of up to 4 carbon atoms, preferably 1 to 2 carbon atoms; and by lower cycloalkyl, it is meant that R' may be cycloalkyl of from 5 to 8 carbon atoms, preferably 5 or 6 carbon atoms. As suitable representative examples of non-toxic water soluble cations represented by $M^+$ in the foregoing formula, there may be mentioned alkali metals, ammonium, and hydroxyalkyl substituted ammonium. Suitable N-acyltaurates are available commercially, such as sodium N-methyl-N-cocoyl taurate, for example, under the trade designation IGEPON TC-42 from the GAF Corporation of New York. The taurate component preferably comprises N-methyl-N-cocoyl taurate in an amount from about 15 to about 25 percent by weight of the paste formulation.

A skin conditioner is provided to impart a smooth and soft feeling to the skin surface, and to inhibit drying of the skin by reducing water loss from the stratum corneum. The skin conditioner must not affect the essential properties of the cleansing agent formulation, i.e. latherability, defoamability, detergency, rinseability, and the like. Lecithin, e.g. soybean lecithin, has been found to be a suitable skin conditioner in combination with N-methyl-N-cocoyl taurate as the foaming detergent component. Other skin conditioners contemplated as being suitable in the present formulation include, for example, long chain fatty acids; liquid water-soluble polyols; glycerin; propylene glycol; sorbitol; polyethyleneglycol; alkoxylated ethers of methyl glucose; alkoxylated ethers of lanolin alcohol; sodium pyrrolidone carboxylic acid; lactic acid; urea; L-proline guanidine; pyrrolidone; hexadecyl, myristyl, isodecyl, and isopropyl esters of adipic, lactic, oleic, stearic, isostearic, myristic, and linoleic acids; hydrolized protein and other collagen-derived proteins; aloe vera gel; acetamide methylethanolamine; petrolatum; mineral oil; bees wax; silicones; lanolin and oil soluble lanolin derivitavies; saturated and unsaturated fatty alcohols such as behenyl alcohol, squalene; squalane, various animal and vegetable oils such as almond oil, peanut oil, wheat germ oil, linseed oil, jojoba oil, oil of apricot pits, walnuts, palm nuts, pistachio nuts, sesame seeds, rape seed, cade oil, corn oil, peach pit oil, poppyseed oil, pine oil, castor oil, soybean oil, avocado oil, safflower oil, coconut oil, hazelnut oil, olive oil, grape seed oil, sunflower seed oil and the like.

The skin conditioner is present in an amount effective to condition the skin, preferably from about 0.1 to about 3 percent by weight of the formulation. If insufficient skin conditioner is used, the paste formulation may dry out the skin over a period of time, whereas there is generally no additional benefit obtained and extra load is placed on water reduction equipment when excessive amounts of conditioner are employed.

It has also been found that certain particularly preferred skin conditioners, such as, for example, lecithin, can enhance the foaming characteristics of the taurate compound.

As suitable hair conditioners there may be mentioned polymeric quaternary ammonium salts such as the quaternary ammonium salt of hydroxyethyl cellulose, copolymers of dimethylaminoethyl methacrylate and acrylamide, copolymers of dimethyldiallyl ammonium chloride and acrylamide, cationic starches and the like. Polyquaternium 16 obtained under the trade designation LUVIQUAT FC-500 has been found to be suitable.

The hair conditioning agent is present in the paste formulation in an amount effective to condition the hair, preferably from about 0.1 to about 3 percent by weight of the formulation.

A suitable preservative is generally one which preserves the paste formulation from oxidation, microbial growth and the like, but a preservative which alters body flora is not acceptable. Contemplated exemplary preservatives include, for example, methylparaben, propylparaben, formaldehyde, imidazolidinyl urea, ethylenediamine tetraacetic acid, and the like. These preservatives are generally present in an effective amount, preferably from about 0.01 to about 1 percent by weight of the paste formulation.

The paste formulation may additionally contain relatively minor amounts of buffer, e.g. sodium chloride, unreacted precursor components, impurities, and the like which do not substantially adversely affect the essential characteristics of the cleansing formulation. The remainder of the whole body cleansing agent comprises water to achieve a suitable paste consistency.

The ingredients of the whole body cleansing agent are generally combined and mixed in any order using conventional equipment and techniques to form a composition of paste consistency suitable for dispensing in microgravity conditions.

The paste of the present invention lends itself to use in bathing procedures wherein it is desired to use a small quantity of water, e.g. less than about 10 liters, and especially less than about 4 liters of water per shower. In general, the bathing method includes wetting the skin and hair with a small quantity of water, lathering the wetted skin and hair with the paste, rinsing the skin and hair with a small quantity of water, and where water reclamation is desired, defoaming the rinse water containing the cleansing agent and supplying the defoamed rinse water to a water reclamation system for recycle thereof.

This bathing process is typically effected using a whole body cleansing system which includes a pressurized water source, means for wetting and rinsing the skin and hair with water from the water source, means for dispensing the paste, means for recovering water and the paste from the skin and hair, means for defoaming the recovered water, and means for supplying the defoamed water to a water reclamation unit for recycling. Water from a pressurized water source can be used to wet the skin and hair, for example, using a suitable quick-activated, hand-held valve having a high-pressure/low throughput nozzle on the end of a flexible water supply line feeding the pressurized water thereto. After wetting the skin, the paste is dispensed from a suitable hand operated pump, squeeze tube or the like, as are commonly used for dispensing pastes, such as, for example, toothpaste. If desired, the paste-dispensing means may be adapted for delivery of a premeasured quantity of the paste. Commercially available dispensers include, for example, the REALEX HVD high viscosity dispenser manufactured by Calmar, Inc. of New Jersey and similar dispensers described in U.S. Pat. No. 4,511,068 which is hereby incorporated herein by reference.

After the paste is worked into a lather on the wetted skin and hair, it is generally rinsed using the wetting and rinsing means, e.g. the hand-held valve described above. The rinse water containing the foam and any soil removed therewith, may be recovered by conventional means such as a drain under gravity conditions, or by using a vacuum source to collect the foam and rinse water directly from the skin under microgravity conditions. If desired, the vacuum source may be combined with the water dispensing means into a single hand-held unit wherein the vacuum source is introduced to the lather/rinse water using a similar quick-activated, hand-held valve at the end of a flexible hose in fluid communication with the vacuum source.

The lather/rinse water mixture recovered under microgravity conditions is preferably defoamed using conventional anti-foaming agents added thereto in a conventional manner. The anti-foam agent commercially available from Dow Corning under the trade name 536 Fluid has been found to be a suitable defoamer at a concentration below 100 ppm, e.g. 10 ppm. The defoamed rinse water is then treated in a cyclone separator to remove entrained air, and supplied to a water reclamation unit adapted to remove impurities, for example, by distillation, freezing, reverse osmosis, ion exchange, ultrafiltration, etc., and recycle the reclaimed water to the high pressure water source.

The invention is illustrated by way of the following examples.

EXAMPLE 1

A paste formulation according to the present invention was prepared by combining and mixing together the following ingredients in the stated proportions:

| COMPONENT | PERCENT BY WEIGHT |
| --- | --- |
| 1. GEPON TC-42 (sodium N-methyl-N-coconut acid taurate 24 wt. %) | 98.65 |
| 2. LECIPUR 95-F (soybean lecithin) | 0.50 |
| 3. LUVIQUAT FC-500 (polyquaternium 16) | 0.75 |
| 4. FORMALIN (37 wt. % formaldehyde) | 0.10 |

The pH of the paste formulation was adjusted to 6.1 with hydrochloric acid. A 3.8 liter (one gallon) shower was built to supply pressurized water on the spray nozzle fitted with the hand-held quick-opening valve. The pressurizing means was a small centrifugal pump having an output fitted with a flexible tubing connector and flexible tubing. The other end of the flexible tubing was connected to the hand operated spray nozzle. A water reservoir with a 3.8 liter capacity supplied water to the pump. The formulation was evaluated by six people consisting of four adult men and two adult women of normal proportions. The water supply was distilled and heated to 49° C. The whole body cleansing formulation was squeezed from a tube with the tube weighed prior to and after utilization to determine an amount used. Each person taking the shower applied the cleansing agent and water in a manner comfortable to each. The shower included a shampooing of the hair. Results of the cleansing agent and water usage are as follows:

Average amount of water used—3.0 liters/shower

Average amount of cleansing agent—4.3 grams/shower Comments from the participants regarding the effects of the cleansing agent included good foamability, soft feeling of the lather, good rinsability and clean feeling to the skin following rinsing. No negative comments were expressed about the cleansing formulation. Evaluations on humans in a 3.8 liter (one gallon) shower showed the formulation to be mild and effective.

EXAMPLE 2

Approximately 10 ppm of Dow Corning Fluid 536 anti-foam agent is added to the water recovered from bathers using the formulation of Example 1. The recovered water is satisfactorily defoamed.

The foregoing description is illustrative and explanatory only, and it is readily apparent that various modifications and variations will occur to those skilled in the art in view thereof. It is intended that all such variations and modifications which fall within the scope or spirit of the appended claims be embraced thereby.

I claim:

1. A method of bathing with a small quantity of water, comprising the steps under microgravity conditions of:

wetting the skin and hair with a small quantity of water;
   lathering said wetted skin and hair with a whole body cleansing agent comprising a formulation of paste consistency consisting essentially of:
   (i) N-acyl taurate of the formula $R-C(O)-NR'-CH_2-CH_2-SO_3^-$ $M^+$ wherein RCO is aliphatic acyl of from about 6 to about 20 carbon atoms, R' is hydrogen, lower alkyl or lower cycloalkyl, and $M^+$ is a non-toxic water soluble cation in an amount effective for cleaning hair and skin using a small quantity of water;
   (ii) a conditioner or conditioners in amounts effective for conditioning the skin and hair; and
   (iii) a preservative in an amount effective to preserve said taurate and said conditioner or conditioners;
   rinsing said lather from said skin and hair with a small quantity of water to produce a rinse water containing said cleaning agent;
   aspirating said rinse water from said skin and hair;
   defoaming said rinse water; and
   supplying said defoamed rinse water to a water reclamation unit for recycle thereof, said steps effectively cleansing said skin and hair with a maximum quantity of about 10 liters of water.

2. The method of claim 1, wherein said R is alkyl of from about 9 to about 17 carbon atoms.

3. The method of claim 1, wherein R' is hydrogen, methyl or cyclohexyl.

4. The method of claim 1, wherein $M^+$ is ammonium, lithium, sodium or potassium.

5. The method of claim 1, wherein said taurate comprises N-methyl-N-cocoyl taurate.

6. The method of claim 1, wherein said taurate comprises from about 15 to about 25 percent by weight of said paste.

7. The method of claim 1, wherein said conditioner comprises lecithin present in an amount of from about 0.1 to about 3 percent by weight of said paste.

8. The method of claim 1, wherein said conditioner comprises a polymeric quaternary ammonium salt in an amount of from about 0.1 to about 3 percent by weight of said paste.

9. The method of claim 1, wherein said conditioners comprise from about 0.1 to about 3 percent by weight lecithin and from about 0.1 to about 3 percent by weight of a polymeric quaternary ammonium salt.

10. The method of claim 1, wherein said preservative is formaldehyde present in an amount of from about 0.01 to about 1 percent by weight of said paste.

11. The method of claim 1, wherein said water reclamation unit comprises an air/water cyclone separator.

* * * * *